United States Patent [19]

Friis

[11] Patent Number: 5,035,713
[45] Date of Patent: Jul. 30, 1991

[54] SURGICAL IMPLANTS INCORPORATING RE-ENTRANT MATERIAL

[75] Inventor: Elizabeth A. Friis, Wichita, Kans.

[73] Assignee: Orthopaedic Research Institute, Inc., Wichita, Kans.

[21] Appl. No.: 478,433

[22] Filed: Feb. 12, 1990

[51] Int. Cl.$^5$ .......................... A61F 2/28; A61F 2/30; A61F 2/36; A61F 2/54

[52] U.S. Cl. .......................................... 623/16; 623/8; 623/13; 623/17; 623/18; 623/20; 623/23; 623/66

[58] Field of Search ............... 623/1, 2, 11, 13, 16–18, 623/20, 66, 8, 22–23

[56] References Cited

U.S. PATENT DOCUMENTS

| | | | |
|---|---|---|---|
| 3,605,123 | 4/1969 | Hahn | 623/16 |
| 3,852,045 | 12/1974 | Wheeler et al. | 623/66 X |
| 3,855,638 | 12/1974 | Pilliar | 623/16 |
| 4,017,911 | 4/1977 | Kafesjian et al. | 623/2 |
| 4,101,984 | 7/1978 | MacGregor | 623/2 |
| 4,206,516 | 6/1980 | Pilliar | 623/16 |
| 4,351,069 | 9/1982 | Ballintyn et al. | 623/16 X |
| 4,355,426 | 10/1982 | MacGregory | 623/2 X |
| 4,542,539 | 9/1985 | Rowe, Jr. et al. | 623/16 |
| 4,668,557 | 5/1987 | Lakes | 623/1 UX |

Primary Examiner—Ronald Frinks
Attorney, Agent, or Firm—Kokjer, Kircher, Bradley, Wharton, Bowman & Johnson

[57] ABSTRACT

The use of re-entrant foam material as implants is disclosed. The re-entrant foam material may comprise the entire implant or other material may be used as a substrate with either a portion of the implant made of re-entrant material or a coating of re-entrant material may be applied or bonded to the substrate.

8 Claims, 2 Drawing Sheets

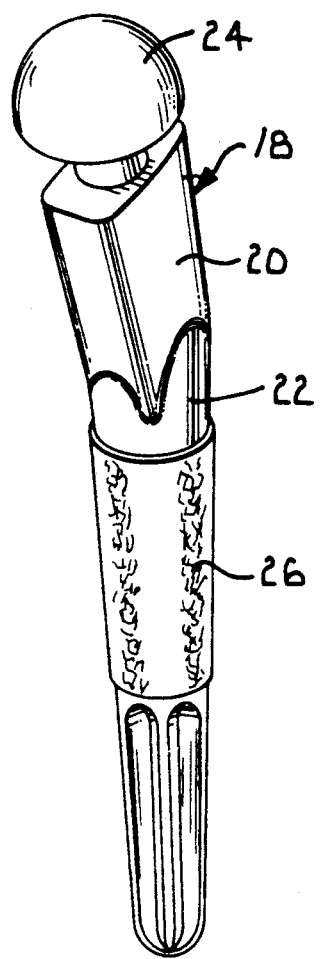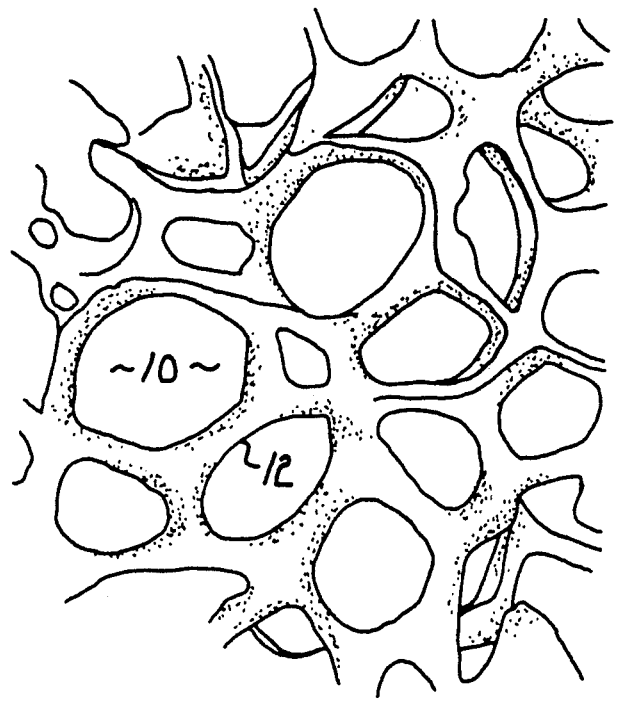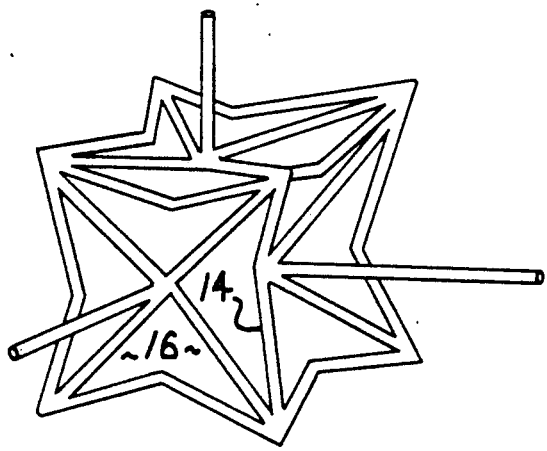
Fig. 1.
Fig. 2.
Fig. 3.

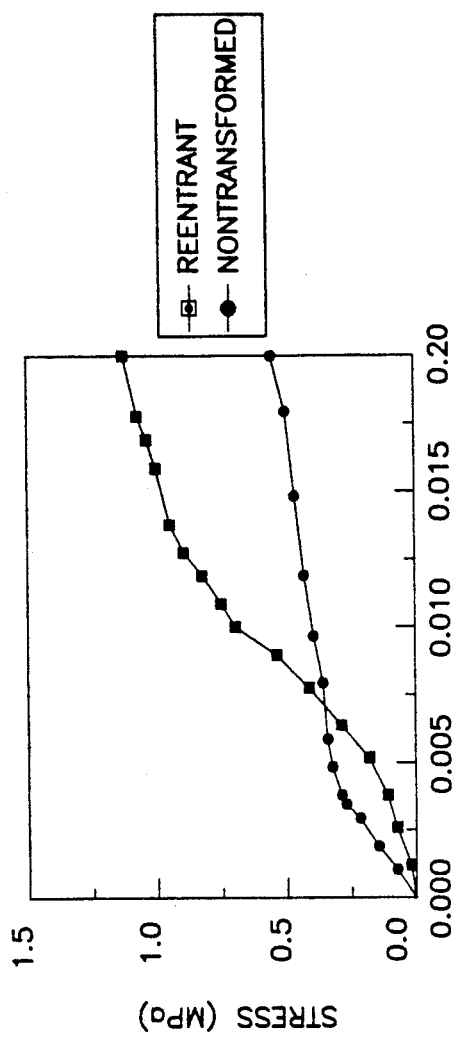
Fig. 6.
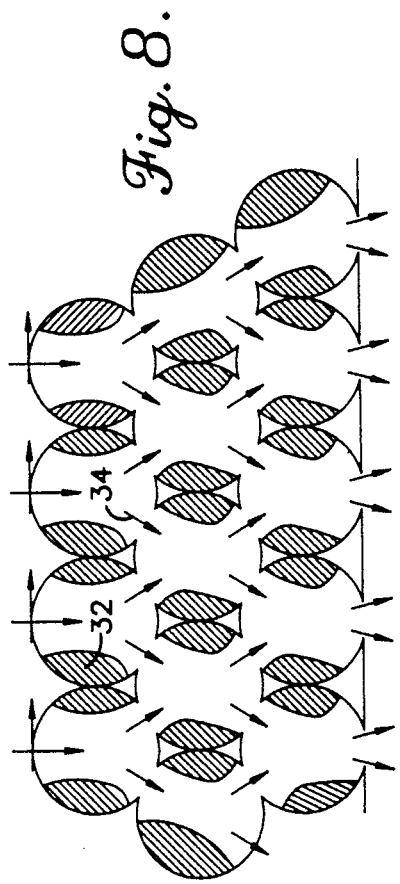
Fig. 8.
Fig. 5.
Fig. 4.
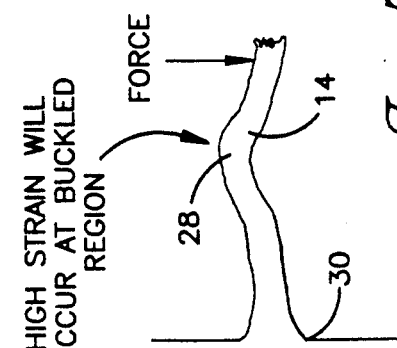
Fig. 7.

SURGICAL IMPLANTS INCORPORATING RE-ENTRANT MATERIAL

BACKGROUND OF THE INVENTION

This invention relates generally to the field of surgical implant devices and in particular to surgical implants either made entirely of a porous material or from other material but having at least one margin of a porous material. The porous material contemplated by this invention may be any biocompatible metal, polymeric or composite material having the characteristics which have been denominated "re-entrant".

The characteristics of re-entrant structure were taught by R. S. Lakes in U.S. Pat. No. 4,668,557 issued May 26, 1987. The present invention involves the discovery that the use of such material in connection with surgical implants enhances the biological attachment of particular types of implants and prolongs viability of these implants. The surgical implant applications contemplated by the invention include especially those applications involving dynamic loading conditions and those applications where tissue ingrowth is desired. Under dynamic loading conditions, the implants of this invention minimize damage to surrounding tissue that would otherwise be caused by improper load distribution such as has been characteristic for prior implants.

The re-entrant structure is a variant of a polyhedral cell structure. The structure is perhaps most conveniently made from open cell foamed materials, but other methods of making them have been contemplated. The Lakes U.S. Pat. No. 4,668,557 referred to above describes methods of making re-entrant structures. The disclosures of the '557 patent are hereby incorporated herein by reference.

Foamed polyhedral cell structures are well known. The individual cells in the foam may be generally open or they may be almost uniformly closed, but in any variation, a plurality of inter-connected cells are referred to as foam. The unqualified word "cells" usually refers to closed cells with faces or walls forming each distinct cell. The intracellular space is thus usually defined by real boundaries formed by the walls or faces of the cell.

Instead of having completely solid walls or faces, open cells have structural members which can be called struts or ribs. These struts constitute the edges and corners of the polyhedral cells. Adjacent cells are, therefore, open to each other having only common edges and corners. The boundaries between open cells are imaginary boundaries defined by the imaginary walls connecting the struts. The cell's imaginary boundary walls define the cellular space.

This invention contemplates the use of relatively hard, generally stiff or rigid, and at least partially open-celled, foam material wherein a significant number of the struts or ribs which define the cell buckle inwardly or "re-enter" the intracellular space defined by the ribs in a unbuckled configuration. Terms such as "re-entrant structure", "re-entrant foam", or "re-entrant material" refer to foam structures with the inwardly buckled configuration. This configuration offers unique advantages over the porous materials employed with surgical implants in the past.

Re-entrant material is characterized by a network of intercommunicating channels of free space. The dimensions of the space can be varied to form any desired width and shape. This free space can be thought of as pores, intracellular space, or communicating channels and its dimensions are referred to as cell width or pore size, which are terms used interchangeably herein.

The advantages achieved by this invention derive from the unique construction of the material employed by the invention, i.e., ribs or struts of biocompatible, metal or polymeric or composite, and the inwardly buckled, "re-entrant", configuration of a significant number of the ribs. The re-entrant structure is formed by tri-axial compression of a normal open-celled reticulated foam such that a 20 to 40 percent permanent compression of the macroscopic (outside) dimensions is attained in the resulting structure. It has been shown that the mechanical behavior of the foam, that is the initial and final apparent modulus of elasticity and Poisson's ratio, can be largely controlled by the amount of transformation compression used to create the re-entrant foam from the parent foam. The re-entrant foam has greater density and strength than the parent foam. Thus a parent foam, of insufficient strength and otherwise unsuitable to be incorporated into implant devices, is transformed into a re-entrant foam material that is suitable for this purpose.

Relatively rigid re-entrant material possesses unique load bearing characteristics that are especially useful under dynamic loading conditions and make such material useful for implants and prosthetic devices exposed to dynamic loading conditions, and/or movement. Simultaneously, the foam offers a superior porous matrix for the ingrowth of bone and/or fibrous tissue. In addition, the re-entrant foam provides means of varying porosity, load bearing ability, and other characteristics more conveniently than the porous coatings utilized in the past.

Particular ranges of pore width can be conveniently manufactured to suit the needs of particular applications. This feature is useful because it is known that the type of tissue ingrowth in a porous medium can be controlled by selection of pore size. This is desirable, for example, to achieve successful implantation for cosmetic applications that, in the past, have proved unsuccessful. Therefore, this invention encompasses such advantages as the ability to control the type of tissue ingrowth desired according to the necessities of a particular implant application.

This combination of desirable features makes re-entrant structures very useful materials for the construction of devices to be surgically implanted into the musculoskeletal system especially and other applications where implanted devices are exposed to loads and movements of living organisms.

The material is even more particularly useful for the construction of orthopaedic implant devices. Implant devices of special interest include, but are not limited to, devices such as the components employed in vertebral disc prosthesis (constructed of rubber-like plastic polymer) hip and knee arthroplasty (adapted to traditional styled implant devices), meniscus repair, other joint repair devices, and other implants that may or may not utilize bone cement; bone substitutes such as those employed as augments in autogenous grafting procedures and those employed as bone or soft tissue extensions in cosmetic surgery.

The term "implant" as used herein also includes, but is not limited to devices used to repair tendons and ligaments. The invention contemplates employing re-entrant material into any implanted device where biological attachment is desired. A given application may call for re-entrant material made from any biocompatible substance including but not limited to pure metals, metal alloys, polymers, composites and the like.

Tissue ingrowth is often a preferred means of fixing an implant to biologic structures or tissues surrounding the implant. Porous materials having the appropriate pore size permit tissue ingrowth and therefore biologic attachment of the implanted device. The invention can employ this feature to either attach the implant in such a fashion as to prolong the useful life of the implant or to enable selective ingrowth of soft tissue for the purpose of obtaining a desired result such as, for example, breast implant devices.

In the past, varied methods for obtaining a porous margin on surgical implant devices have been employed. Material was often added to the surface of the body of the implant so that a layer or coating of porous material could interface with the biologic tissue. Types of coatings varied from plasma sprayed coatings to spherical metal beads or fibers sintered together to form a porous layer.

Conventional technology teaches the manufacture of porous coatings by bonding together a plurality of discrete particles, such as metal beads or fibers, at their points of contact with each other to define a plurality of connected interstitial pores in the coating. The bonds between the beads are known to have a tendency to break apart after implantation. This produces the undesirable result that particles are released into the surrounding tissue and useful life of the implant may be decreased. Uneven and inefficient stress distributions are also inherent to the multiple particle composition. No one, insofar as the applicant is aware, has suggested the use of inherently contiguous re-entrant structures having the desired feature of porosity as a means for overcoming these disadvantages.

A deficiency of prior biologically attached implants has been the stress concentrations created where the coating and the implant substrate meet. These concentrations of stress are caused by the geometry of the coating, i.e., the spherical beads and round fibers have limited contact with the flat surface of the implant substrate which forms a sharp crack where the two meet. This sharp crack greatly increases local stress in the substrate and will lead to premature implant fatigue failure by gradual propagation of the crack leading to complete fracture of the implant.

Another deficiency of prior biologically attached implants is the ability of porous coating to transfer load to the surrounding and ingrowing bone tissue. Present coating art, i.e., beads and fibers, do not have the ability to deform and conform to the shape of the cavity into which the implant is inserted. This nonideal fit can result in localized pressure necrosis of the surrounding bone which can lead to weakening and loss of the bone. The new ingrowing bone spicules can also be damaged and growth inhibited by strain incompatibilities between the bone and the stiffer porous coating.

U.S. Pat. No. 3,855,638 issued to Pilliar on Dec. 24, 1974 teaches the necessity of controlling the interstitial pore size and coating porosity within critical limits in the construction of implants. This patent also teaches that variations between the critical limits may be made depending on the requirements of individual applications. However, neither this patent nor other prior art has suggested a convenient means of controlling these parameters.

Prior structures have characteristically suffered from other inherent deficiencies. Such structures uniformly employ an undesirable trade off ratio of effective pore volume and load carrying ability. Of the porous structures heretofore employed, none have enabled the desired optimization of both effective pore volume and load carrying ability at the same time. For instance, sintered beads do not optimize either usable pore volume or material distribution. The large portion of the material lies outside the load transfer pathways and merely adds weight and decreases needed pore volume.

In the past only relatively cumbersome means of exerting generally limited control over the ratio of effective pore volume and load carrying ability has been known. Furthermore, only limited ability to vary these characteristics according to the needs of implants for the variety of surgical applications has been available. For example, the qualities desired for implant devices used in total hip arthroplasty differ from the qualities desired for a tibial plateau for a total knee prosthesis. Heretofore, the ability to vary these characteristics according to the needs of different locations and biological loading has been extremely limited and the means of accomplishing this variation extremely cumbersome.

The re-entrant material of the instant application is newly designed for optimal application to the task of promoting tissue ingrowth for biologic fixation of implants while improving strength characteristics. Lakes taught that a re-entrant structure exhibited a controllable negative Poisson's ratio, superior abrasion resistance, and an initial apparent modulus of elasticity lower than the parent (non-reentrant) foam. A fundamental proposition of engineering mechanics holds that at a load bearing transition from one material to another (e.g., from the porous implant layer to bone) the stresses in the transition zone will be lowered as the modulus difference between the two materials decreases. This is often called modulus matching. Since bone, especially new bone, has a much lower elastic modulus than any current porous metallic coating, the use of a re-entrant coating with its lower initial apparent modulus of elasticity will represent a considerable advance toward modulus matching and will lower the overall bone stresses near the surface of the implant. The invention of this application simultaneously contemplates the desirable advantages of high effective pore volume and good load carrying ability together with reduced local stress concentrations that make rigid re-entrant materials particularly useful in implant devices requiring strength and bone or fibrous tissue ingrowth.

The Lakes U.S. Pat. No. 4,668,557 taught only the use of re-entrant material for effecting the fastening together of two components in a structure by employing its desirable quality of lateral expansion on stretching. The negative Poisson's ratio of such material necessarily implies expansion under tensile loading conditions. By contrast, essentially all other materials and foam structures have a positive Poisson's ratio and are noted for their lateral contraction on stretching. As for the re-entrant structure's utility in implantation devices, Lakes only disclosed that the feature of resiliency in an artificial blood vessel comprised of a re-entrant structured material might be designed to more closely match the feature of resiliency of the natural blood vessel, particularly the elastic response of arteries to pressure pulses in the flowing blood. Lakes did not suggest the use of rigid re-entrant foams to improve implantation devices by enhancing their biological fixation, their strength, their stress distributing properties, and the other features discussed herein.

SUMMARY OF THE INVENTION

It is an object of the invention to provide a re-entrant structure material suitable for use as a porous medium capable of promoting tissue ingrowth for the attachment of implants. The re-entrant material used in this application can be selected from a group comprising a wide variety of materials such as metals, metal alloys, polymers and composites having appropriate mechanical properties that are also compatible with biologic tissues. Materials such as polyethylene, polyethylene teraphthalate, polypropylene, polysulfone, polylactic acid and polydioxanone are considered useful for this purpose.

It is an object of the invention to provide an implant comprising a body coated with, laminated with, or otherwise structurally associated with re-entrant material to enhance selected tissue ingrowth.

Another object of the invention is to provide an implant device consisting entirely of the re-entrant material capable of promoting selected tissue ingrowth into multiple locations.

Another object of the invention is to provide a convenient means for varying the features of load bearing character, tissue ingrowth, and coating/body interface strength to suit various applications and to suit various conditions of a single application.

A further object of the invention is to provide material for an implant device wherein the moduli of elasticity, i.e., initial apparent modulus of elasticity and final apparent modulus of elasticity, may be designed to match the biological tissues surrounding it so as to minimize damage to those tissues.

A further object of the invention is to provide an implant device for bone tissues comprised of re-entrant material of initial apparent moduli of elasticity designed to match the surrounding bone so as to maximize load sharing with surrounding bone.

A still further object of the invention is to provide a device comprised of re-entrant material having prolonged life due to increased resistance to fatigue.

Among the advantages of the use of rigid re-entrant foams for implant devices contemplated by the instant invention are reduced stress enhancement, prolonged fatigue life, relatively low exposed surface area, ease of control of pore size and distribution, control of apparent modulus of elasticity, control of Poisson's ratio, improved stress distribution, improved fatigue resistance, improved strain distribution, improved material distribution and greater load carrying abilities.

BRIEF DESCRIPTION OF THE DRAWINGS

FIG. 1 is a side elevational view of an implant device having a layer of re-entrant material secured to its outer surface.

FIG. 2 is a fragmentary, enlarged cross-sectional representation of an idealized cell of a typical open cell foam showing the prominent structural features of the interconnecting cellular spaces defined only by the struts.

FIG. 3 is a fragmentary, enlarged perspective view of an idealized open cell having the re-entrant configuration showing the characteristic inwardly buckled struts.

FIG. 4 is an enlarged, fragmentary, idealized representation of a substrate re-entrant coating interface.

FIG. 5 is a representation similar to FIG. 4 but showing a substrate bead coating interface.

FIG. 6 is a typical stress-strain diagram for a metallic re-entrant (transformed) structure and its parent (non-transformed) porous metal illustrating the change in apparent modulus of elasticity with deformation.

FIG. 7 is an enlarged, fragmentary substrate/re-entrant interface illustrating the response of a typical re-entrant strut to strain.

FIG. 8 is a schematic illustration showing the inefficient material utilization in typical beaded porous coatings.

DESCRIPTION OF THE PREFERRED EMBODIMENT OF THE INVENTION

A cell 11 of a typical open cell foam material is illustrated generally in FIG. 2 of the drawing. The open spaces 10 are defined by interconnected ribs or struts 12 which are shown in the idealized representation as relatively straight. As explained in U.S. Pat. No. 4,668,557, a characteristic of such material is a positive Poisson's ratio.

Also as explained in U.S. Pat. No. 4,668,557, a foam material as shown in FIG. 2 can be transformed into a material having a cell structure as is ideally illustrated in FIG. 3 by following the steps described in detail in that patent and as have been summarized herein. A significant number of the ribs or struts 14 which define the respective open spaces or cell pores 16 are bent to "re-enter" the respective pores. Structures of this kind are usually characterized by a negative Poisson's ratio and such a structure is termed re-entrant structure or material. However, it is also possible to achieve a desired value of Poisson's ratio (e.g., positive ratio in tension with negative ratio in compression, zero Poisson's ratio, etc.) in the manufacture of re-entrant foam material.

This invention contemplates a novel use of re-entrant material in the construction of surgical implants as discussed herein. Such use can, of course, take many possible forms to achieve the aforestated benefits to be derived from the use of re-entrant material in connection with implant technology.

FIG. 1 of the drawing illustrates one manner of the use of this material in carrying out the objectives of this invention A prosthesis 18 is representative of any of a variety of orthopaedic devices which might, for one medical purpose or another, be desired to be implanted in a human or another animal. In this case, the relatively rigid load bearing body 22 of the prosthesis includes an elongated shaft 20 having a surface presenting a substrate adapted to be inserted in a hollow portion of a bone, and a sphere 24 mounted on the body 18 to provide a portion for a skeletal joint. Prostheses of this type are commonly composed of metal such as titanium alloys, stainless steel, cobalt-chromium alloys, or other suitable metals.

Conventionally, a prosthesis of the kind illustrated in FIG. 1 would be provided with some sort of porous coating in the region at which a strong bond with the bone is desired so that growth of the bone into the porous coating would effect the bond. However, pursuant to the principles of the present invention, the conventional porous coating is omitted and a coating 26 of re-entrant material, such as a layer of the material, is affixed by any suitable means in relationship to the surface substrate shaft of 20. The size and location of coating 26 is chosen to facilitate the ingrowth of adjacent bone to effect the desired bond between the prosthesis and the bone at the most biologically appropriate location. Further, additional coatings 27 of re-entrant material may be affixed in similar fashion if desired.

It should be pointed out at this juncture that the embodiment of the invention illustrated in FIG. 1 is representative only. Those skilled in the art will readily recognize that the invention may take many forms wherein an implant may be partially or entirely constructed of re-entrant material, rather than merely provided with a re-entrant coating applied to a solid material substrate. The particular manner employed for carrying the invention into effect will depend on the end results sought to be achieved by or for the implant.

Whether the re-entrant structured material is employed as a stand alone implant device or as an improved porous medium for incorporation into implant devices of more than a single material, the re-entrant structure provides means for improved attachment of implants by tissue ingrowth. For this type of application, metals, polymers, and composites are prime choices for fabricating the re-entrant structure. However, the reticulated re-entrant structure could be made from any type of material that provides sufficient strength and biocompatibility for a given application.

The interstitial pore size of the re-entrant structure can be varied according to the type of tissue ingrowth desired. For example, if bony tissue ingrowth is desirable for the specific application, a structure can be prepared having an average interstitial pore size in the range of about 100 microns to about 1000 microns. Often a range of about 150 to about 600 microns may be selected for this purpose. Likewise, if only fibrous tissue ingrowth is desired, a structure with somewhat smaller (less than 100 microns) average interstitial space would probably be appropriate and can be prepared. In addition, the pore size can be conveniently varied from one portion of the implant to another, possibly enabling for the first time prosthetic devices with locations for muscle attachments and also enabling bone segment or even total bone replacement.

Control over the interstitial space of the pores in the re-entrant structure is achieved by simply selecting the pre-transformation pore size of the re-entrant structure's parent foam and the amount of tri-axial compression applied. For instance, in one preferred embodiment an average diameter pore size can be compressed to achieve a 50 micron size. Of course the precise means for varying pore size and shape depends on the method employed for achieving the foam structure.

The process used to create the re-entrant structure may or may not vary depending on the type of material selected. Any creation/transformation process which results in a suitable re-entrant structure could be used in this application.

The use of the re-entrant structure as a porous coating on implant devices or as a stand-alone medium for tissue ingrowth has several advantages over previously used mediums for tissue ingrowth. The initial modulus of elasticity and the final apparent modulus of elasticity (FIG. 6) of the re-entrant structure can be controlled to more nearly match that of the tissue with which it is in contact. For example, if bony ingrowth is desired, the modulus of the re-entrant foam can be matched to the modulus of the particular bone at the location of the implant. Once presented with a load, this matching minimizes local spicule damage that would otherwise occur with the bone and implant having mismatched moduli. Also with matched moduli of elasticity, load sharing by the implant with immediately surrounding bone is uniform.

The useful life of the metallic re-entrant structure is superior to that of previous structures used for tissue ingrowth such as Titanium and Cobalt-Chromium sintered beads or powders and Titanium fiber metal pads. FIGS. 5 and 4 illustrate in representative fashion the substrate/coating interfaces for beads and re-entrant structure respectively. The beads in FIG. 5 have high stress concentrations at the bead/substrate interface due to the sharp crack-like radii at the contact point of the bead and substrate. At the points 50 where the particles are bonded to each other and, more importantly, where they are bonded to the prosthetic substrate 52, bridging necks are formed. The external radii of these necks are extremely small (typically 2/10,000 of an inch) and act like tiny undercuts in the bead-substrate connection. The tip radii of these undercuts are so small, in fact, that they act like cracks which, under repetitive loading, readily propagate into the neck to release a bead or into the substrate to produce the fatigue failures to which porous coated implants are susceptible.

This problem should be completely avoided with re-entrant structures. As shown in the re-entrant structure illustrated in FIG. 4, the attachment of the foam to the prosthesis is achieved by a gradual increase of the rib or strut cross-section until it blends smoothly into the substrate. The re-entrant structure attachment to the prosthesis 40 is horn or bell shaped such that no small radius undercuts are formed. It is considered that elimination of the small neck radii of the bead and wire coatings will substantially improve the fatigue resistance of porous coated implants. Consequently, the device avoids early fatigue failures and has an increased useful life.

After a critical strain is reached, the re-entrant structure should be able to withstand high loading conditions with lower resulting deformations than conventional porous structures. In other words, the re-entrant structure becomes stiffer with greater loads. Damage to ingrown bone from deformation in this range is thus minimized. Greater stiffness results from the increasing apparent modulus of elasticity of the re-entrant structure with increasing deformation and load once the critical strain is reached. FIG. 6 illustrates a typical stress-strain diagram of a metallic re-entrant structure. This diagram illustrates the change in apparent modulus of the re-entrant structure with load and deformation.

Poisson's ratio of the re-entrant structure can be controlled. The ratio can differ under differing load conditions. In compression, the magnitude and sign of the ratio can differ from the magnitude and sign of the ratio in tension. Control over this ratio enables control of individual device responses under varying applications. For example, in applications in which expansion under compression is undesirable but expansion under tension is desirable such as intermedullary rods or bone graft augmentation, the re-entrant structure may be fabricated to exhibit a negative Poisson's ratio in tension and little Poisson's effect in compression.

With a negative ratio in tension, the device tends to expand and grip the surrounding tissue when placed in tension. This provides more stabilization in shear and torsion as well. Because the implant does not expand under the more frequent compression loading, there is reduced incidence of tissue necrosis which would otherwise result from the expansion pressure on the surrounding bone. These varying interactions can provide a more natural dynamic fixation and should reduce the adverse stress effects of a stiff implant. Another example of a variation in Poisson's which could be beneficial is to fabricate the re-entrant structure to exhibit a zero Poisson's ratio. With a Poisson's ratio equal to zero, there should be less micromotion which can break fragile tissue interconnections. An example of where this may be desirable is the tibial plateau portion of a total knee prosthesis, where many types of forces are acting which tend to disrupt the interface.

In another situation, it is desirable to transfer loads to the tissue and maintain implant stability under all loading configurations (tension, compression, shear, and torsion). In this case, a re-entrant structure is fabricated to exhibit a positive (or zero) Poisson's ratio in compression and negative in tension. In this way, the re-entrant structure expands transversely under every type of loading. Total hip arthroplasty is one situation in which this arrangement is beneficial.

In another application, a highly flexible, polymeric re-entrant structure could be used for implants imbedded in soft tissue either as a coating or as the complete implant. Examples would include breast augmentation prostheses and defect filling, such as is required after ablative surgery for tumors. Implants of this kind would be improved by the stabilizing tissue ingrowth into their surfaces because shifting of a free floating implant due to muscular activity and external forces can cause chafing of the surrounding tissue. This chafing provokes the proliferation of a fibrous encapsulation of the implant Over time, this capsule can become stiff and even hard, detracting markedly from the cosmetic appearance and compliance of the reconstruction. Attempts to coat these implants with porous textile coatings such as velours have had limited success because collapse and matting of the textile fibers inhibits ingrowth. Re-entrant polymeric structures with controllable elastic modulus and Poisson's ratio can be tailored for these soft tissue applications by making the structure just stiff enough to remain open to tissue ingrowth, but as soft as possible and consistent with ingrowth, to match the stiffness of the soft tissue.

It is important to note that re-entrant structure is an inherently contiguous structure, i.e., it is not particles with weak interconnections like other structures used for tissue ingrowth such as sintered metal beads or fibers. Thus the re-entrant structure is less likely to break apart after implantation and release particles into the surrounding tissue. In addition, because re-entrant material is inherently contiguous, a more even stress distribution exists at the substrate/coating interface, as illustrated generally in FIG. 7. The majority of the strain in the coating is at the buckled region 28 of the strut 14 as shown in FIG. 7, thus the structure shields strain from regions with higher stress concentrations (such as the coating/substrate attachment point 30). This reaction occurs not only at the coating/substrate interface but also throughout the coating thickness. Accordingly, the likelihood of crack propagation either down to the substrate or throughout the coating is reduced.

When re-entrant material is used as a porous coating, the total area of attachment of the material at the coating/substrate interface is much greater than with previously used coatings. This increased attachment area (therefore increased shear strength) provides superior attachment to the substrate as compared to beads, for example.

As discussed above, the pore size, shape, and distribution of the re-entrant structure can be easily controlled, thus making it less difficult to achieve the optimum configuration for a specific tissue ingrowth situation. Specifically, the standard deviation of the average interstitial space in re-entrant material is low. This is important since the range of pore space appears to be a controlling factor in the type of tissue which will grow in. Further, the pathway of the interstitial spaces is direct, i.e., the tissue does not have to weave around very much to achieve fixation. These advantages are especially apparent as compared to the previously used beads in porous coatings. Along the same lines, the surface area of the re-entrant structure coating to which the biological environment is exposed is much less than that which is exposed with conventional bead porous coatings. This reduced surface area decreases the rate of toxic ion release by slow corrosion of the implant metal.

The re-entrant structure is very efficient in that it maximizes the free and appropriate size range pore volume available for ingrowth while minimizing stress concentrations within the porous material itself. That is, the material is distributed in such a way that all the struts in the re-entrant structure carry load. By contrast, other porous mediums, such as sintered beads, do not optimize either usable pore volume or material distribution in such a way that the majority of the medium material lies mainly along the load transfer pathways. FIG. 8 illustrates schematically this inefficient material distribution. In this figure, the unused material (i.e., the material which serves little load carrying ability) of the respective beads 31 are represented by the crosshatched portions 32. The load trajectories are represented by the arrows 34. Compared to bead coatings, very little non-functional material is present in the re-entrant structure coating.

The low-strain region elastic modulus of the re-entrant structure when used as a coating generates relatively reduced stresses and reduced long term local pressure necrosis when the implant is press fit as compared to the conventional porous coatings. For this reason, the re-entrant coating allows for more forgiveness of surgical error. For instance, the low-strain elastic modulus of the re-entrant structure coating will make immediate damage of the surrounding bone less likely in a press fit implant. More particularly, in coating will be more likely to deform and not split or crack the bone or cause regional pressure necrosis.

The re-entrant structure may be fabricated to have gradations in porosity such that a more dense structure could be formed near the attachment to the substrate. In this way, a greater shear strength is easily attained at the substrate/coating interface. Distant from the coating/implant interface, the structure can be made less dense, resulting in a lower modulus and a better match to the stiffness of the surrounding tissue.

The overall cost of fabrication and production of implants with a re-entrant structure coating should be reduced as compared to more conventional porous coatings such as sintered beads. This follows from the fact that fewer production steps are necessary and the material costs are comparatively lower.

Although the embodiments described mainly refer to use of a re-entrant material to provide a porous coating on a substrate for biological fixation, other applications of the re-entrant structure involving tissue ingrowth are evident. For example specifically shaped bone block substitutes in reconstructive surgery are readily evident.

It is the intention of the inventor that these and other tissue ingrowth applications and other surgical implant applications be included within the scope of the following claims.

Having thus described the invention, I claim:

1. An orthopaedic device to be surgically implanted in living tissue to become functionally attached to said tissue, said device comprising:
   a relatively rigid, load bearing body having a surface presenting a substrate;
   a layer of re-entrant structure on said substrate in disposition for ingrowth of said tissue into the re-entrant structure for attaching the layer to the tissue,
   said re-entrant structure comprising an open-cell material having a negative Poisson's ratio in at least one direction and under at least one mode of deformation and having a plurality of interconnected, spaced apart ribs defining a plurality of cells, the ribs being partially buckled and at least some of said buckled ribs protruding inwardly of the cells; and
   means fixedly securing the re-entrant structure layer to said substrate to effect attachment of the body to the tissue.

2. A device as set forth in claim 1, wherein the average size of the cells of said re-entrant material is less than 100 microns.

3. A device as set forth in claim 1, wherein the average size of the cells of said re-entrant material range from about 150 microns to about 1000 microns.

4. A device as set forth in claim 1, wherein the re-entrant material is a transformed foam made of material selected from the group consisting of stainless steel, titanium alloys, elemental titanium and chromium-cobalt alloys.

5. A device as set forth in claim 1, wherein the re-entrant material is a transformed foam made of material selected from the group consisting of polyethylene, polyethylene teraphthalate, polypropylene, polysulfone, polylactic acid, and polydioxanome.

6. A device as set forth in claim 1, wherein the re-entrant material is a transformed foam made of polymer material which is biologically compatable with human tissue.

7. A device as set forth in claim 1, wherein the density of said re-entrant material is greater proximal said substrate than proximal said tissue.

8. A device as set forth in claim 1, wherein the re-entrant material is formed from the same material as the substrate.

* * * * *